United States Patent
Kieft

(10) Patent No.: US 8,446,502 B2
(45) Date of Patent: May 21, 2013

(54) TIME DOMAIN MULTIPLEXING FOR IMAGING USING TIME DELAY AND INTEGRATION SENSORS

(75) Inventor: Erik Rene Kieft, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 13/255,285

(22) PCT Filed: Mar. 8, 2010

(86) PCT No.: PCT/IB2010/050978
§ 371 (c)(1),
(2), (4) Date: Sep. 8, 2011

(87) PCT Pub. No.: WO2010/103448
PCT Pub. Date: Sep. 16, 2010

(65) Prior Publication Data
US 2011/0317052 A1  Dec. 29, 2011

(30) Foreign Application Priority Data
Mar. 10, 2009  (EP) .................................... 09305221

(51) Int. Cl.
*H04N 3/14* (2006.01)
*H04N 5/228* (2006.01)
*H01L 27/00* (2006.01)

(52) U.S. Cl.
USPC ...................... 348/295; 348/222.1; 250/208.1

(58) Field of Classification Search
USPC .............................. 348/295, 222.1; 250/208.1
See application file for complete search history.

(56) References Cited

U.S. PATENT DOCUMENTS

| 4,954,900 | A  | * | 9/1990  | Frame ........................... 348/317 |
| 5,990,503 | A  | * | 11/1999 | Ingram et al. .................. 257/236 |
| 7,113,651 | B2 |   | 9/2006  | Liang |
| 7,342,658 | B2 |   | 3/2008  | Kowarz |
| 2003/0048933 | A1 |   | 3/2003 | Brown |
| 2003/0218746 | A1 |   | 11/2003 | Sampas |
| 2006/0018013 | A1 |   | 1/2006 | Suzuki |
| 2010/0046853 | A1 | * | 2/2010 | Goodnough et al. ......... 382/275 |

FOREIGN PATENT DOCUMENTS
WO  03042644 A1  5/2003

* cited by examiner

*Primary Examiner* — Nhan T Tran
*Assistant Examiner* — Marly Camargo

(57) ABSTRACT

A time delay integration (TDI) sensor (22) comprises a sequence of cells (42, 44, 42, 44) numbered 1 to N. The TDI sensor is configured for transferring a charge from the cell numbered 1 via the cells numbered 2 to N−1 to the cell numbered N. Each cell (42; 44) in the sequence of cells is either sensitive or insensitive in the sense that when the TDI sensor (22) is evenly illuminated by light (46) having a first spectrum, the intensity of the light (46) incident on any of the insensitive cells (44) is at most 90% of the intensity of the light (46) incident on any of the sensitive cells (42). The sequence of cells (42, 44, 42, 44) comprises, in this order: a first sensitive cell (42), at least one insensitive cell (44), and a second sensitive cell (42). An imaging system comprising a TDI sensor and a method of imaging an object are also disclosed.

15 Claims, 4 Drawing Sheets ized to be used in a time domain multiplexing TDI
TIME DOMAIN MULTIPLEXING FOR IMAGING USING TIME DELAY AND INTEGRATION SENSORS

FIELD OF THE INVENTION

In a first aspect, the invention relates to a time delay integration (TDI) sensor comprising a sequence of cells numbered 1 to N, the TDI sensor being configured for transferring a charge from the cell numbered 1 via the cells numbered 2 to N-1 to the cell numbered N.

In a second aspect, the invention relates to an imaging system.

In a third aspect, the invention relates to an imaging method.

BACKGROUND OF THE INVENTION

In fluorescence imaging, there is often a need for detecting the presence of multiple fluorescent labels (fluorophores) in a given sample simultaneously. Various methods may be employed to discriminate fluorescent labels.

In a first method, light emitted by the labels is split over multiple detectors according to wavelength, for instance, by using dichroic mirrors.

Another method uses the fact that different labels are usually sensitive to different wavelengths of light for excitation. A set of light sources, e.g. lasers, differing in their respective wavelengths, is operated in an alternating manner. Each of the light sources typically excites a particular set of fluorescent labels. Separate images of the various labels can be obtained by reading out each detector before switching to the next light source, i.e. before changing the frequency of the illumination light. The technique is an example of time sharing or time domain multiplexing. An advantage is that it allows using one detector for detecting light of different frequencies. The technique thus avoids the need for providing a separate detector for each wavelength.

The two methods can be combined so as to increase the number of fluorophores that are detectable using a fixed number of light sources. It is noted that the total number of fluorophores that can be detected independently may be larger than both the number of different light sources and the number of detectors.

In a scanning microscope with time domain multiplexing, the total integration time per scan is increased as compared to detecting a single type of fluorophore per sensor. However, time domain multiplexing is still advantageous over doing multiple scans of the same area for at least two reasons. Firstly, less time is lost to 'overhead' for scanning the sample (for, e.g., reversing the scan direction or moving the sample back to a start position for the next scan). Secondly, changes in the system over time have less influence on a mutual alignment of images obtained from different excitation and/or fluorescence wavelength.

Time domain multiplexing is suitable, among others, for confocal scanning (using, for example, non-pixelated sensors), simple line sensors and full frame sensors. In the case of a line sensor and a continuously moving sample, the light sources are usually switched every time the pixel rows have been read out, so that after a single scan two or more different full images of the same object have been acquired.

Time delay and integration (TDI) is an imaging method known to be often faster compared to using a simple line sensor. It can be applied both to brightfield and other imaging modalities. TDI typically uses a special charge coupled device (CCD) having multiple adjacent rows of pixels. As an image of the object is scanned continuously over the sensor, the accumulated charge on the sensor is moved in a synchronous manner from each row of pixels to the next row. Each time, only a signal from the last row of pixels is read out and stored in memory. In this way a signal is accumulated on the sensor with a much longer integration time than is possible on a simple line sensor at the same scan speed.

In summary, for various applications of scanning fluorescence imaging it is often considered advantageous to detect multiple fluorophores on an object under study simultaneously. To this end, multiple light sources emitting light at different wavelengths can be employed. The light sources can be operated so as to expose the object to light at different wavelengths in an alternating fashion. A sensor detecting fluorescent light from the object may be read out between two consecutive illumination periods.

FIG. 1 illustrates the principle of TDI imaging. An object 12 is illuminated by a light source (not shown) and moved with constant speed along an object path 14. In the Figure, only an exemplary light-emitting point of the object 12 is graphically represented. Imaging optics 20 comprising, for example, a lens or a lens system, generates an optical image 24 of the object 12 on a TDI sensor 22. As the object 12 moves along the object path 12, its image 24 moves across the TDI sensor 22 along an image path 26. In the example shown, the object path 14 is a straight line, but other paths may be envisaged, depending on the design of the TDI sensor 22. In the example shown, the image path 26 is also a straight line. Note that the object 12 and its image 24 move in opposite directions, as indicated by the arrows 14, 26. The sensor 22 comprises a plurality of parallel rows 28, each row comprising a plurality of pixels (cells). The rows 22 comprise a first row 30 and a last row 32. While the object 12 is located at an initial position as shown in the Figure, light 16 emitted by the object 12 is incident on the first row 30. As the object 12 is at a final position (corresponding to the tip of the arrow 14), light 18 emitted by the object is incident on the last row 32 of the sensor 22. Charge is accumulated on the pixels of the TDI sensor 22 as a function of both the intensity of the optical image 24 and the time during which the pixels are exposed to the image 24. The accumulated charge is shifted through the sensor 22 synchronously with the movement of the optical image 24. The signal built up by the sensor 22 is therefore larger than that of an equivalent simple line sensor by a factor that equals the number of pixel rows 22. During two consecutive readouts of the TDI sensor 22 the object 12 moves over a scan length that can be quite considerable in comparison to the size of the features of interest of the object 12. A problem, however, is that switching between imaging modes, such as switching of light sources, before reading out the entire TDI sensor 22 would result in mixing of the corresponding images on the sensor 22.

It is an object of the invention to provide a time domain multiplexing TDI imaging method. It is another object of the invention to provide a time domain multiplexing TDI imaging system. It is yet another object of the invention to provide a TDI sensor for being used in a time domain multiplexing TDI imaging system.

These objects are achieved by the features of the independent claims. Further specifications and preferred embodiments are outlined in the dependent claims.

SUMMARY OF THE INVENTION

According to the first aspect of the invention, each cell in the sequence of cells is either sensitive or insensitive in the sense that when the TDI sensor is evenly illuminated by light having a first spectrum, the intensity of the light incident on any of the insensitive cells is at most 90% of the intensity of the light incident on any of the sensitive cells, and the sequence of cells comprises, in this order: a first sensitive cell, at least one insensitive cell, and a second sensitive cell. The charge may be transferred in consecutive steps, each step involving a transfer of charges such that $$Q_{after}(i+1) = Q_{before}(i) \ (i=1 \text{ to } N-1)$$

where $Q_{before}(i)$ is the charge in the cell numbered i before a shift and $Q_{after}(i)$ is the charge in the cell numbered i after the shift. The cells 1 to N may be identical in construction, in which case they differ only in their position and/or orientation. The first spectrum may in particular be a combined spectrum of multiple light sources, in which case the insensitive cells are "blind" to light emitted by any of the multiple light sources. It is pointed out that the sensitive cells and the insensitive cells may alternatively (or additionally) be characterized by a rate at which a charge is generated in a cell when the TDI sensor is illuminated. More precisely, each of the cells may have associated with it a capacity for holding a charge, and when the TDI sensor is evenly illuminated by the light having the first spectrum, there may be a point in time at which each of the sensitive cells will have accumulated a charge corresponding to at least 50% of its capacity and at which each of the insensitive cells will have accumulated a charge corresponding to at most 40% (preferably at most 20%, or at most 10%, or at most 5%) of its capacity.

The TDI sensor may have associated with it a natural number K larger than 1, such that for any i, i=1 to N-K, the cells are related as follows:

if the cell numbered i is sensitive, the cell numbered i+K is also sensitive, and if the cell numbered i is insensitive, the cell numbered i+K is also insensitive.

The cells are thus configured in a periodic manner. This can be particularly convenient if the TDI sensor is to be illuminated in a periodic manner, for instance by K alternating light sources. For example, the sequence of cells may be designed such that the cell numbered i (i=1 to N) is sensitive if i−1 is an integer multiple of K, and insensitive if i−1 is not an integer multiple of K. The constant K may, for example, be 2, 3, 4, or any other natural number.

The TDI sensor may in particular be designed such that the intensity of the light incident on any of the insensitive cells is zero. In such a configuration, all light is blocked from the insensitive cells.

The TDI sensor may be configured for transferring the charge at discrete instants in time. The discrete instants may be equidistant. This can be convenient when the TDI sensor is to be used in conjunction with one or more periodically pulsed light sources.

The TDI sensor may comprise a plurality of cells arranged in rows and columns, each column comprising a sequence of cells as described above. The columns may be configured identically, in which case each of the rows comprises either only sensitive cells or only insensitive cells. It is pointed out, however, that the plurality cells could be arranged very differently, for instance, along a segment of a circle, or along segments of concentric circles. This could be convenient for scanning an object by rotating the object relative to the TDI sensor.

The sensitive cells may be arranged in a plane. The insensitive cells, or at least some of them, may be arranged in the same plane. Alternatively all or at least some of the insensitive cells may be arranged behind the plane, "behind" referring to the side of the plane that is usually not reached be the incident light. For example, an insensitive cell could be arranged behind a corresponding sensitive cell such that the sensitive cell masks the insensitive cell, at least partially, from the incident light.

The TDI sensor may comprise an opaque element which is opaque at least for light having the first spectrum, the opaque element masking at least one of the insensitive cells but none of the sensitive cells. The opaque element may be reflective or absorbing, or a combination of both. According to a preferred embodiment, the opaque element is opaque for the entire spectrum from the far infrared to the far ultraviolet. According to a different preferred embodiment, the opaque element is transparent for light having higher frequencies or lower frequencies than those contained in the first spectrum. For detecting such light, the TDI sensor could be used as a conventional TDI sensor.

Alternatively or additionally, the TDI sensor may comprise an optical element for focusing light having the first spectrum on at least one of the sensitive cells but on none of the insensitive cells. More particularly, the optical element may be configured for focusing an incident plane wave having a frequency belonging to the first spectrum.

The optical element may comprise a cylindrical lens or an array of lenses, for focusing the light on at least two sensitive cells. As mentioned above, the cells may, for example, be arranged in rows and columns, each row comprising, for example, either only sensitive cells or only insensitive cells, cells of distinct rows belonging to distinct sequences (i.e., charges are transferred along the columns, not along the rows). Rows comprising only sensitive cells, and rows comprising only insensitive cells may be referred to as sensitive rows and insensitive rows, respectively. In this case it may be particularly convenient to arrange a cylindrical lens in front of each sensitive row, for focusing incident light on the respective row and for preventing at least an important portion of the incident light from reaching insensitive rows.

The above introduced sequence of cells may be a first sequence and the TDI sensor may comprise a second sequence of cells numbered 1 to N, the TDI sensor being configured for transferring a charge from the cell numbered 1 via the cells numbered 2 to N-1 to the cell numbered N, wherein each cell in the second sequence of cells is either sensitive or insensitive in the sense that when the TDI sensor is evenly illuminated by light having a second spectrum, the intensity of the light incident on any of the insensitive cells in the second sequence is at most 90% (preferably at most 10%) of the intensity of the light incident on any of the sensitive cells in the second sequence, wherein the second sequence of cells comprises, in this order: a first sensitive cell, at least one insensitive cell, and a second sensitive cell, and wherein the cells in the first sequence are not responsive to light having the second spectrum while the cells in the second sequence are not responsive to light having the first spectrum. The TDI sensor may thus comprise at least two sequences of cells of the kind discussed above, differing however in their spectral response. Thus different spectra or different "colors" could be detected simultaneously but independently.

The imaging system according to the second aspect of the invention comprises a TDI sensor as described above with regard to the first aspect of the invention;

an optical system for illuminating the object and for guiding light from the object onto the TDI sensor, the optical system having at least a first mode and a second mode;

a controller for synchronizing the TDI sensor and the optical system such that the TDI sensor shifts the charge from an insensitive cell to a sensitive cell when the optical system assumes the first mode and from a sensitive cell to an insensitive cell when the optical system passes from the first mode to another mode.

The imaging system may further comprise a scanner for moving the object relative to the TDI sensor. The scanner may be configured for translating the object relative to the TDI sensor along a straight path. A speed associated with the object's motion may be constant while the object is scanned.

The optical system may further comprise
a first light source for emitting light having a third spectrum, and
a second light source for emitting light having a fourth spectrum differing from the third spectrum.

The light having the third spectrum and the light having the fourth spectrum may, for example, comprise different frequency components or be differently polarized. Note that the first spectrum and the second spectrum introduced above relate to detection characteristics of the TDI sensor, whereas the third spectrum and the fourth spectrum relate to the light for illuminating the object. In particular for applications such as fluorescence imaging, where the light to be imaged has other frequency components than the light with which the object is illuminated, it may be advantageous to adapt the detection system to the fluorescent light, in which case, and of course not only in this case, the first spectrum (and/or the second spectrum) may differ from the third spectrum (and/or the fourth spectrum). Alternatively, the third spectrum and/or the fourth spectrum may be identical to the first spectrum or to the second spectrum.

The TDI sensor may be a first TDI sensor and the imaging system may comprise a second TDI sensor of the type described above, the first TDI sensor and the second TDI sensor differing in their spectral response. Thus different frequencies could be imaged using different TDI sensors, in combination with time domain multiplexing of different illumination modes.

According to the third aspect of the invention, the method of imaging an object comprises
moving the object relative to a TDI sensor as described above with regard to the first aspect of the invention;
wherein the method further comprises the successive steps of
illuminating the object and guiding light from the object onto the TDI sensor, using a first mode;
transferring an accumulated charge to an insensitive cell;
illuminating the object and guiding light from the object onto the TDI sensor, using a second mode;
transferring the charge to a sensitive cell.

The steps of illuminating the object and of transferring the charge may be repeated until the charged has reached the last cell in the sequence. After the charge has reached the last cell, the last cell may be read out, for example, by converting the amount of the charge into a voltage. Thus the advantages of TDI sensor-based time delay integration methods may be combined with those of time domain multiplexing. The technique may allow building up two different images of the object on the sensor during a single scan.

In this context, guiding light from the object onto the TDI sensor may include forming an optical image of the object on the TDI sensor; the method may then include transferring the charges in accordance with the motion of the image on the TDI sensor.

DESCRIPTION OF PREFERRED EMBODIMENTS

Figure 1:
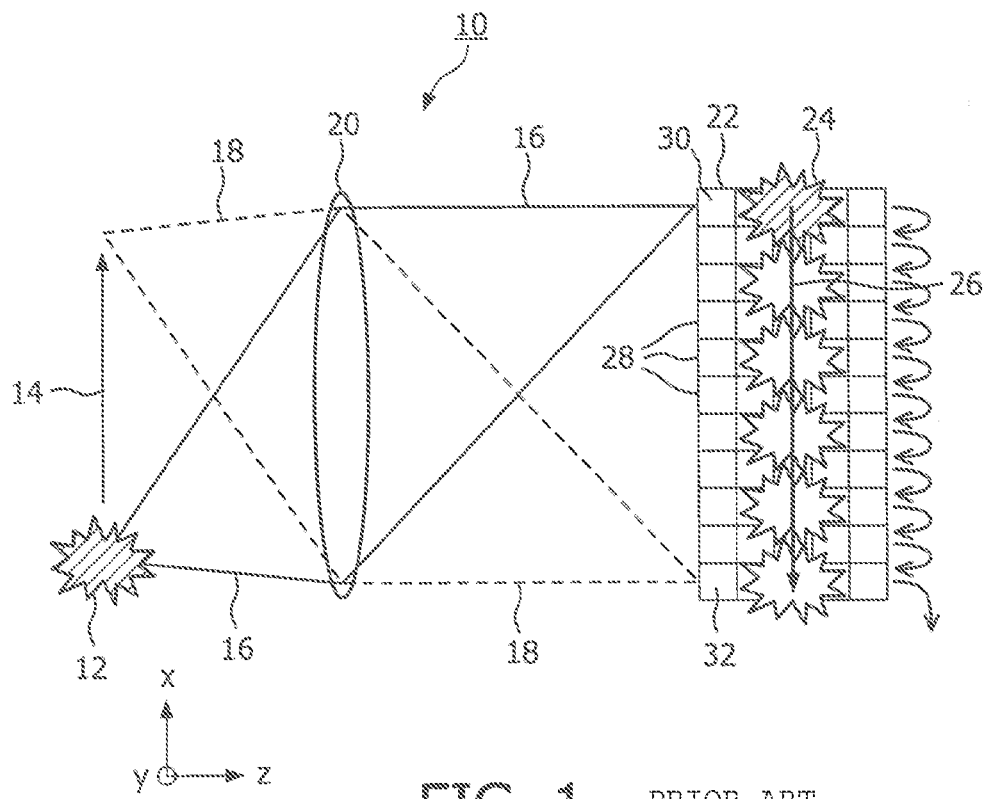
FIG. 1 is a schematic top view of an example of a TDI imaging system.

Unless specified otherwise, identical or similar reference numerals appearing in different Figures refer to identical or similar components.

Figure 2:
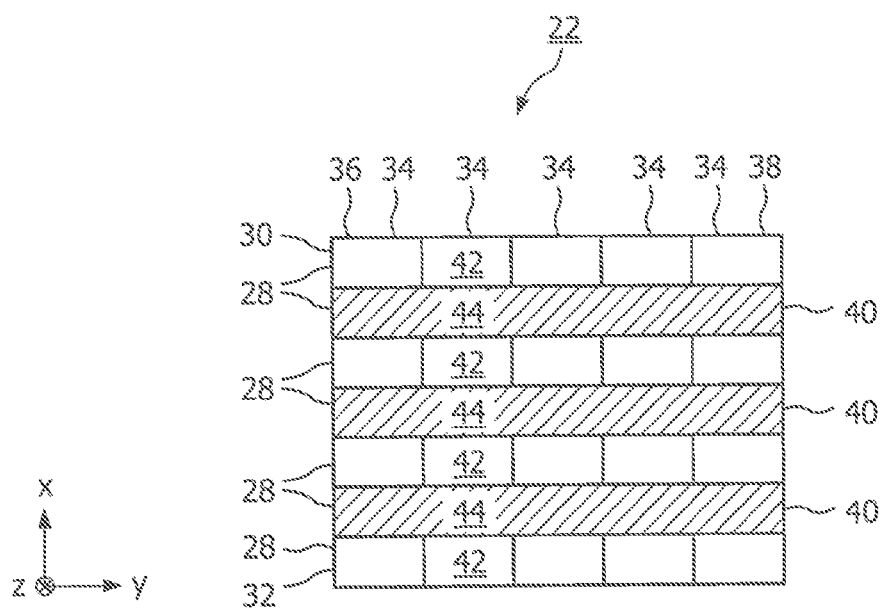
FIG. 2 is schematic front view of an example of a TDI sensor.

FIG. 2 schematically represents a front view of a TDI sensor 22. Each small rectangle represents an individual pixel (cell) of a CCD. The TDI sensor 22 comprises in particular a sequence of cells 42, 44, 42, 44, 42, 44, 42 numbered 1 to N. In the example shown, N=7. In practice the number of cells in the sequence is typically much larger. The sensor is configured for shifting a charge from the cell numbered 1 (the top cell 42 in the Figure, in the first row 30) via the cells numbered 2 to N-1, to the cell numbered N (the lowest cell 42 in the Figure, in the last row 32). Each cell 42, 44 is either sensitive or insensitive in the sense that when the sensor 22 is evenly illuminated by light having a first spectrum, the intensity of the light incident on any of the insensitive cells 44 is at most 10% of the intensity of the light incident on any of the sensitive cells 42. Although it is preferred that the intensity of the light incident on any of the insensitive cells is as low as possible (e.g. at most 10% or at most 20% of the intensity of the light incident on any of the sensitive cells), the methods described in this application could still work properly as long as the intensity of the light incident on any of the insensitive cells is noticeably lower than the intensity of the light incident on any of the sensitive cells if the TDI sensor is evenly illuminated. Note that an even illumination of the TDI sensor is assumed here merely for the purpose of characterizing the cells. In practice, the TDI sensor is not evenly illuminated, but exposed to an optical image of an object. In the example, the sequence of cells 42, 44, 42, 44, 42, 44, 42 represents an alternating series of sensitive cells 42 and insensitive cells 44. In the example, the sensitive cells 42 and the insensitive cells 44 are all inherently light-sensitive in the sense that they would accumulate a charge if they were exposed to light of a suitable frequency (wavelength). They are rendered sensitive and insensitive, respectively, by preventing incident light from reaching the insensitive cells 44. To this end, the sensor 22 comprises opaque elements 40 which are opaque for light having the first spectrum and which mask the insensitive cells 44 but none of the sensitive cells 42. Those rows 28 which are covered by one of the opaque elements 40 and those which are not, are also referred to in this application as unexposed rows and exposed rows, respectively, or as sensitive rows and insensitive rows. It is noted that the sensor pixels (cells) have a physical dimension in the scan direction (parallel to the x-axis) that is half their extension in the perpendicular direction (parallel to the y-axis), subsequent rows corresponding to a single image being separated by twice the normal pixel distance. Alternatively, binning of the pixels or subsampling of the image in the perpendicular direction can be done in software. It is further noted that the last cell in the sequence could alternatively be an insensitive cell. Thus a time interval for reading out the last cell and a time interval for exposing the TDI sensor to light could overlap without affecting the quality of the data that is read out.

In a variation of the embodiment discussed above with reference to FIG. 2, a striped color filter replaces the opaque elements 40. The filter provides a mask that blocks only light of certain wavelengths. With such a mask the TDI sensor may for instance be used as a time domain multiplexing sensor for one wavelength range, while it can still work as a 'full' TDI sensor for other wavelengths.

Figure 3:
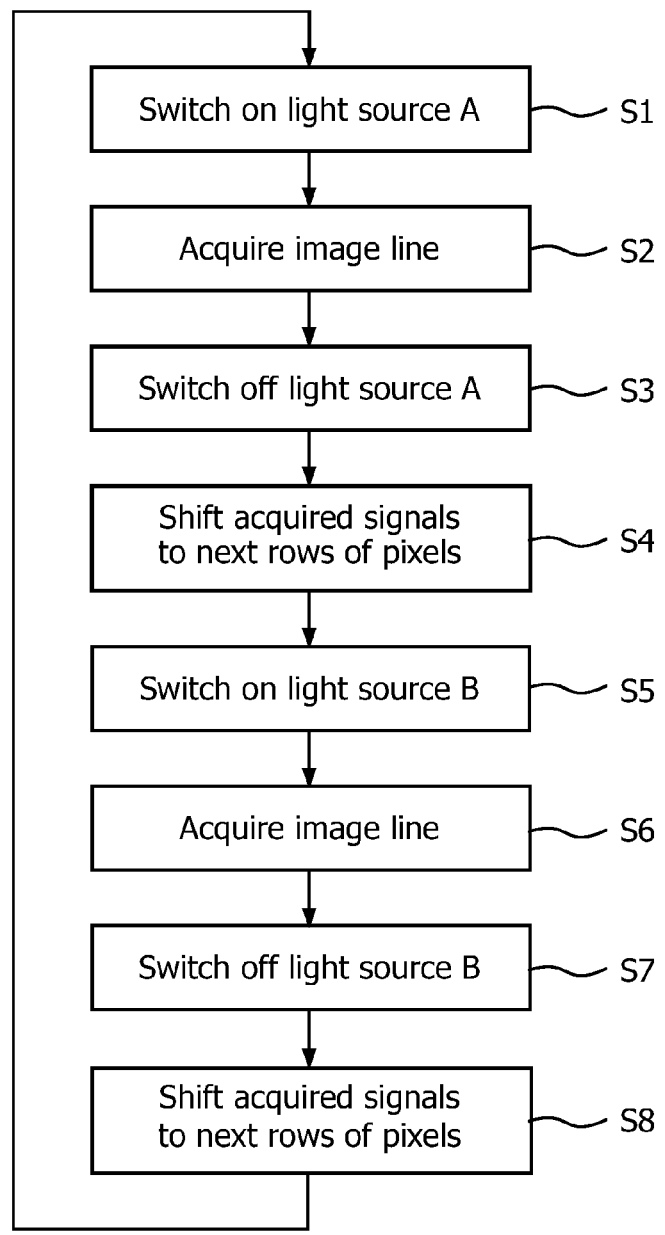
FIG. 3 is a flow chart illustrating steps of an imaging method.

FIG. 3 illustrates a method for acquiring signals on the TDI sensor 22 during a scan of the object 12 shown in FIG. 1, now employing instead of the TDI sensor 22 shown there the modified TDI sensor shown in FIG. 2. It is important to note that the object under study moves at a substantially constant velocity during the scan. First, a first light source ('source A') is switched on (S1). A signal ('image A') is acquired on the sensor roughly for the time it takes the optical image of the object to move over the height of one pixel (S2). Then source A is switched off (S3), all charges on the sensor are moved to the next pixel row (S4), and a second source (source B) is switched on (S5). Again, a signal ('image B') is acquired on the sensor roughly for the time it takes the optical image of the object to move over one pixel (S6). Then source B is switched off (S7), the charges are moved to the next row of pixels (S8), and the whole process (steps S1 to S8) is repeated. Thus the switching of the light sources is synchronized with the transfer of the accumulated charge from each pixel row to the respective next row. An output signal read from the last row of the sensor corresponds to rows of pixels that are related to the different light sources in an alternating manner. De-interlacing the output signal yields two-dimensional images, each related to a different light source.

Figure 4:
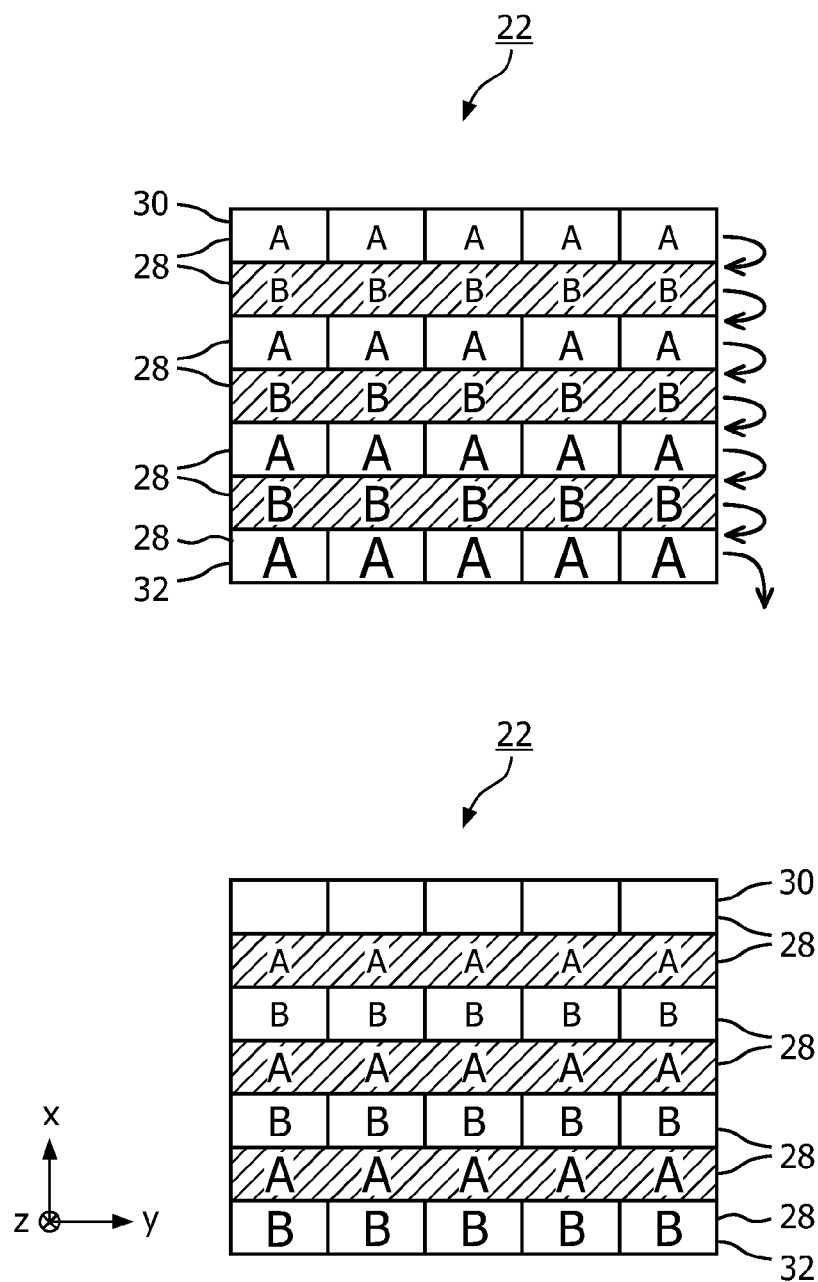
FIG. 4 are schematic front views of an example of a TDI sensor, illustrating two successive states of the sensor.

FIG. 4 illustrates a transfer of charges on the sensor 22 shown in FIG. 2 from one pixel row 28 to the subsequent pixel row 28. The left part of the Figure illustrates the situation just before the charges are shifted. The right part shows the situation after the shift. Before the shift, a part of image A has been built up on the exposed rows (shaded rows 28 in the Figure) of the sensor, in the form of accumulated charges while a part of image B was stored on the unexposed rows (white rows 28 in the Figure). Next, any charges stored on any of the exposed rows are shifted downward to a subsequent unexposed row while any charges stored on the unexposed rows are shifted downward to a subsequent exposed row. Thus, after the transfer, part of image A is stored on the unexposed rows, and part of image B is stored on the exposed rows. The values of the charges in the last row 32 are read out and stored on a computer. Light source B is then switched on to further build up image B on the sensor. If the unexposed rows are not completely shielded from the incident light so that they still receive a portion of the incident light, the original images A and B can still be derived from the values of the charges using image processing.

An extension of the embodiment illustrated with reference to FIGS. 2 to 4 involves more than two light sources. When M light sources are used, only every Mth row is exposed to light, and a cycle of alternating all light sources is matched with the scanning of M rows.

Figure 5:
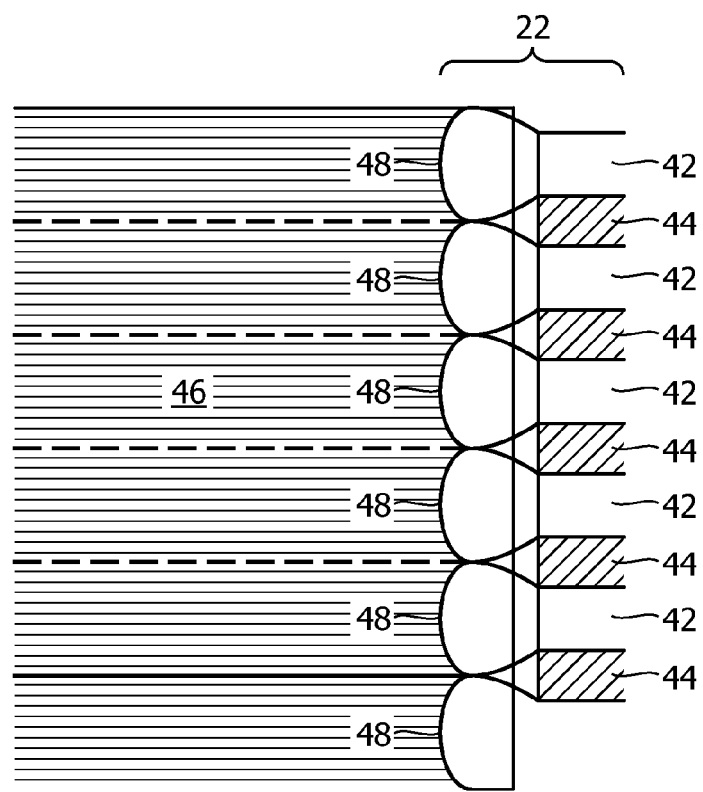
FIG. 5 is a schematic side view of an example of a TDI sensor.

FIG. 5 illustrates a preferred embodiment in which an array of lenses or microlenses is used rather than a simple absorbing or reflecting mask. Shown is a side view of a TDI sensor 22 which is illuminated by a plane wave of light 46. The light 46 is focused by an array of cylindrical lenses 48 onto the rows of sensitive cells 42, leaving no light to fall on the intermediate rows of insensitive cells 44. The cylindrical lenses 48 focus the light 46 only in the scan direction (the x-direction). They thus generate focal lines (extending in the y-direction) instead of customary focal spots. The cylindrical lenses 48 may be further combined with an intensity mask for preventing light from reaching the insensitive cells 44 even more effectively. Alternatively the array of lenses may be a two-dimensional array of spherical focusing lenses.

The current invention may be used for any application involving time domain multiplexing of a TDI sensor. Specifically, it may be applied for fluorescence imaging with multiple fluorophores, for multiple color brightfield imaging, and for combining fluorescence imaging with brightfield imaging in a single scan.

While the invention has been illustrated and described in detail in the drawings and in the foregoing description, the drawings and the description are to be considered exemplary and not restrictive. The invention is not limited to the disclosed embodiments. Equivalents, combinations, and modifications not described above may also be realized without departing from the scope of the invention.

The verb "to comprise" and its derivatives do not exclude the presence of other steps or elements in the matter the "comprise" refers to. The indefinite article "a" or "an" does not exclude a plurality of the subjects the article refers to. It is also noted that a single unit may provide the functions of several means mentioned in the claims. The mere fact that certain features are recited in mutually different dependent claims does not indicate that a combination of these features cannot be used to advantage. Any reference signs in the claims should not be construed as limiting the scope.

The invention claimed is:

1. A time delay integration (TDI) sensor (22) comprising a sequence of cells (42, 44, 42, 44) numbered 1 to N, the TDI sensor (22) being configured for transferring a charge from the cell numbered 1 via the cells numbered 2 to N-1 to the cell numbered N, wherein each cell (42; 44) in the sequence of cells is either sensitive or insensitive in the sense that when the TDI sensor (22) is evenly illuminated by light (46) having a first spectrum, the intensity of the light (46) incident on any of the insensitive cells (44) is at most 90% of the intensity of the light (46) incident on any of the sensitive cells (42), and wherein the sequence of cells (42, 44, 42, 44) comprises, in this order: a first sensitive cell (42), at least one insensitive cell (44), and a second sensitive cell (42).

2. The TDI sensor (22) as set forth in claim 1, having associated with it a natural number K greater than one, such that for any i, i=1 to N-K, the cells are related as follows:
   if the cell numbered i is sensitive, the cell numbered i+K is also sensitive, and
   if the cell numbered i is insensitive, the cell numbered i+K is also insensitive.

3. The TDI sensor (22) as set forth in claim 1, wherein the intensity of the light (46) incident on any of the insensitive cells (44) is zero.

4. The TDI sensor (22) as set forth in claim 1, wherein the TDI sensor is configured for transferring the charge at discrete instants in time.

5. The TDI sensor (22) as set forth in claim 1, comprising a plurality of cells (22) arranged in rows (28) and columns (34), each column comprising a sequence of cells.

6. The TDI sensor (22) as set forth in claim 1, wherein the sensitive cells (42) are arranged in a plane.

7. The TDI sensor (22) as set forth in claim 1, comprising an opaque element (40) which is opaque at least for light (46) having the first spectrum, the opaque element masking at least one of the insensitive cells (44) but none of the sensitive cells (42).

8. The TDI sensor (22) as set forth in claim 1, comprising an optical element (48) for focusing light (46) having the first spectrum on at least one of the sensitive cells (42) but on none of the insensitive cells (44).

9. The TDI sensor (22) as set forth in claim 8, wherein the optical element comprises a cylindrical lens (48) or an array of lenses, for focusing the light (46) on at least two sensitive cells (42, 42).

10. The TDI sensor (22) as set forth in claim 1, wherein the sequence of cells (42, 44, 42, 44) is a first sequence and the TDI sensor (22) comprises a second sequence of cells numbered 1 to N, the TDI sensor being configured for transferring a charge from the cell numbered 1 via the cells numbered 2 to N-1 to the cell numbered N, wherein each cell in the second sequence of cells is either sensitive or insensitive in the sense that when the TDI sensor (22) is evenly illuminated by light having a second spectrum, the intensity of the light incident on any of the insensitive cells in the second sequence is at most 90% of the intensity of the light incident on any of the sensitive cells in the second sequence, wherein the second sequence of cells comprises, in this order: a first sensitive cell, at least one insensitive cell, and a second sensitive cell, and wherein the cells in the first sequence (42, 44) are not responsive to light having the second spectrum while the cells in the second sequence are not responsive to light (46) having the first spectrum.

11. An imaging system (10) for imaging an object (12), comprising
  a TDI sensor (22) as set forth in claim 1;
  an optical system for illuminating the object (12) and for guiding light (16; 18) from the object onto the TDI sensor, the optical system having at least a first mode and a second mode;
  a controller for synchronizing the TDI sensor (22) and the optical system such that the TDI sensor shifts the charge from an insensitive cell to a sensitive cell when the optical system assumes the first mode and from a sensitive cell to an insensitive cell when the optical system passes from the first mode to another mode.

12. The imaging system (10) as set forth in claim 11, wherein the optical system comprises
  a first light source for emitting light having a third spectrum, and
  a second light source for emitting light having a fourth spectrum differing from the third spectrum.

13. The imaging system (10) as set forth in claim 1, wherein the TDI sensor (22) is a first TDI sensor and the imaging system comprises a second TDI sensor, the first TDI sensor (22) and the second TDI sensor differing in their spectral response.

14. A method of imaging an object (12), comprising
  moving the object relative to a TDI sensor (12) as set forth in claim 1;
wherein the method further comprises the successive steps of
  illuminating the object and guiding light (16) from the object onto the TDI sensor, using a first mode;
  transferring an accumulated charge to an insensitive cell (44);
  illuminating the object and guiding light (16) from the object onto the TDI sensor, using a second mode;
  transferring the charge to a sensitive cell (42).

15. The method as set forth in claim 14, wherein guiding light (16) from the object (12) onto the TDI sensor includes forming an optical image (24) of the object on the TDI sensor and wherein the charges are moved in accordance with the motion of the image on the TDI sensor.

* * * * *